United States Patent [19]

Roberts et al.

[11] Patent Number: 5,905,082
[45] Date of Patent: May 18, 1999

[54] CRYSTALLINE OXATHIOLANE DERIVATIVES

[75] Inventors: Tony Gordon Roberts; Paul Evans, both of Ware, United Kingdom

[73] Assignee: Glaxo Group Limited, Greenford, United Kingdom

[21] Appl. No.: 07/892,029

[22] Filed: Jun. 2, 1992

[30] Foreign Application Priority Data

Jun. 3, 1991 [GB] United Kingdom .................. 91 11902

[51] Int. Cl.$^6$ ...................... C07D 411/04; A61K 31/505
[52] U.S. Cl. ............................................. 514/274; 544/317
[58] Field of Search ............................. 514/274; 544/317

[56] References Cited

U.S. PATENT DOCUMENTS

| 5,047,407 | 9/1991 | Belleau et al. | 514/274 |
| 5,179,104 | 1/1993 | Chu et al. | 544/310 |
| 5,204,466 | 4/1993 | Liotta | 544/317 |
| 5,248,776 | 9/1993 | Chu et al. | 544/310 |
| 5,539,116 | 7/1996 | Liotta et al. | 544/317 |

FOREIGN PATENT DOCUMENTS

| 0 382 526 | 8/1980 | European Pat. Off. . |
| 91/17159 | 11/1991 | WIPO . |

OTHER PUBLICATIONS

Solomons, "Organic Chemistry" Fifth Ed. (1992) pp. 1002—1007.

Liotta et al., Chemical Abstracts, vol. 115, entry 208, 463d (1991).

Soudeyns et al., Chemical Abstracts, vol. 115, entry 105523u (1991).

Mansuri et al. Chemtech 1992, p. 564.

Gordon et al. The Chemist's Companion. 1972, pp. 230–233.

Chemical Abstracts, vol. 115, 1991, Columbus, Ohio US; Abstract No. 45942T, p. 486.

R. Rooke et al.: "Biological Comparison of Wild Type and Zidovudine–Resistant Isolates of Human Immunodeficiency Virus Type 1 From The Same Subject", vol. 35, No. 5, 1991, Montreal, pp. 988–991.

Storer et al., *Nucleosides & Nucleotides*, 12(2), 225–236 (1993).

Coates et al., *Antimicrobial Agents and Chemotherapy*, Jan. 1992, 202–205.

Schinazi et al., *Antimicrobial Agents and Chemotherapy*, Mar. 1992, 672,676.

Beach et al., *J. Org. Chem.*, 1992, 57 2217–2219.

*Primary Examiner*—John M. Ford
*Attorney, Agent, or Firm*—Graham & James LLP

[57] ABSTRACT

(−)cis-4-Amino-1-(2-hydroxymethyl-1,3-oxathiolan-5-yl)-(IH)-pyrimidine-2-one in crystalline form, in particular as needle-shaped or bypyramidyl crystals, pharmaceutical formulations thereof, methods for their preparation and their use in medicine.

27 Claims, 3 Drawing Sheets

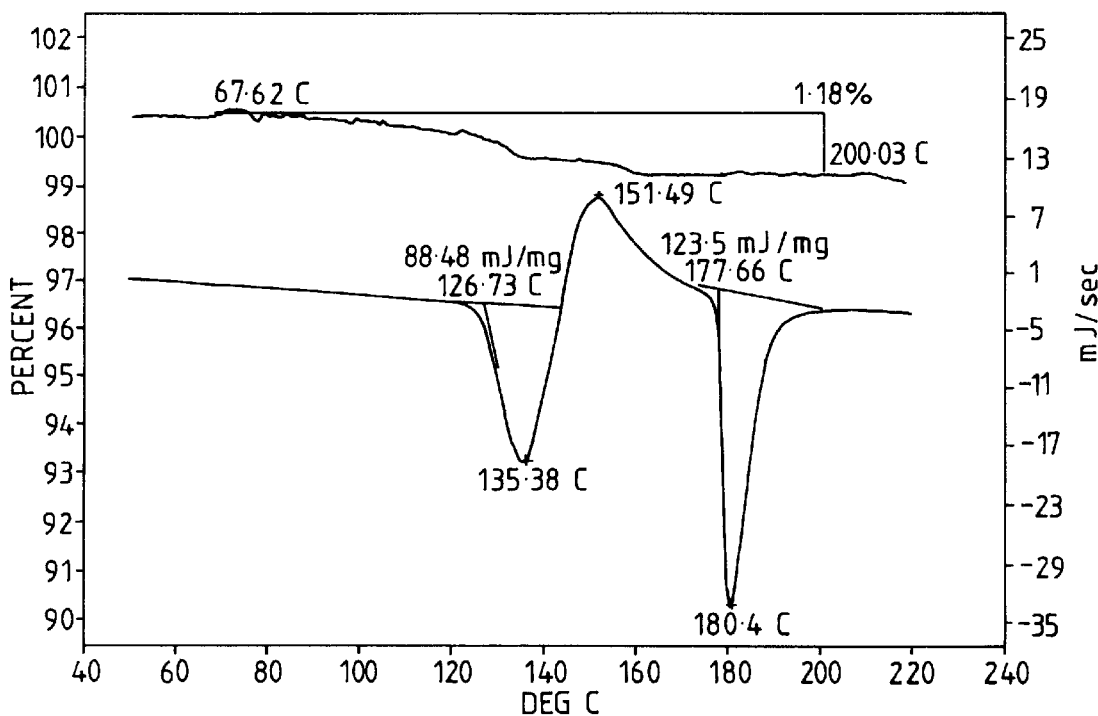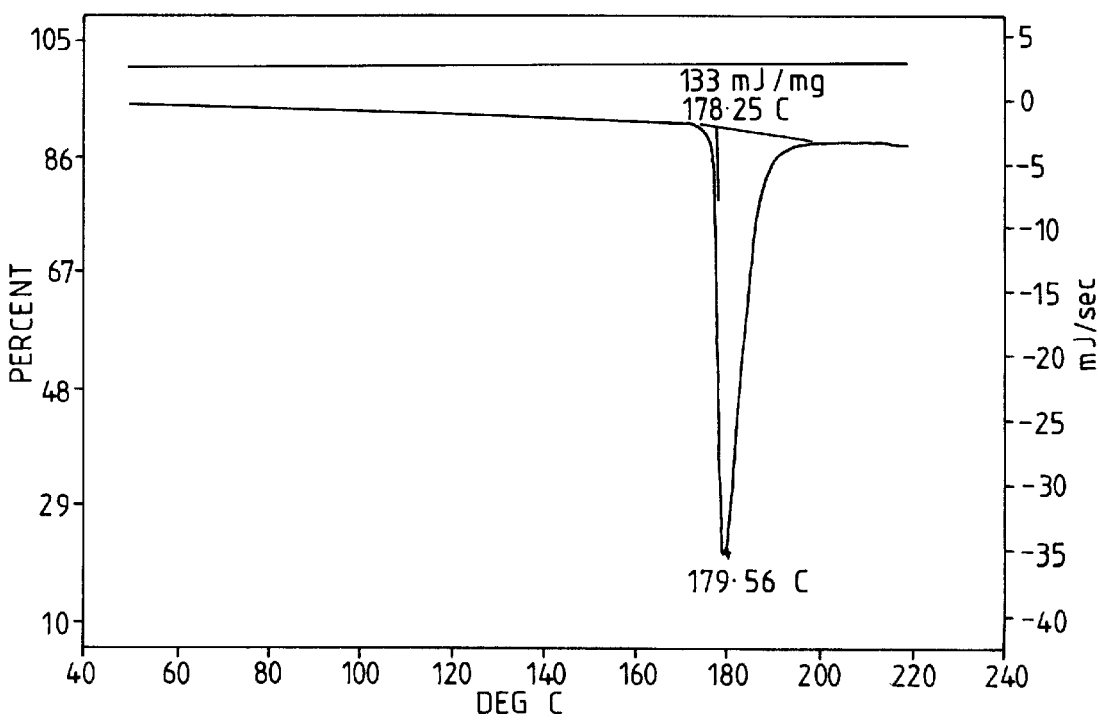

CRYSTALLINE OXATHIOLANE DERIVATIVES

The present invention relates to nucleoside analogues and their use in medicine. More specifically the invention is concerned with 1,3-oxathiolane nucleoside analogues, particular physical form thereof, pharmaceutical formulations thereof and the use thereof in the treatment of viral infections.

The compound of formula (I)

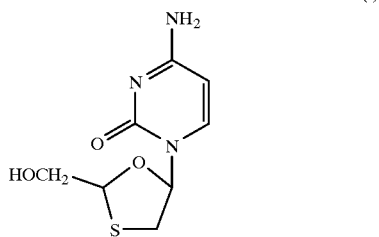

(I)

also known as BCH-189 or NGPB-21 has been described as having antiviral activity in particular against the human immunodeficiency viruses (HIV's), the causative agents of AIDS (5th Anti-Aids Conference, Montreal, Canada 5th–9th June 1989: Abstracts T.C.O.1 and M.C.P. 63; European Patent Application Publication No. 0382562). The compound of formula (I) is a racemic mixture of the two enantiomers of formulae (I-1) and (I-2):

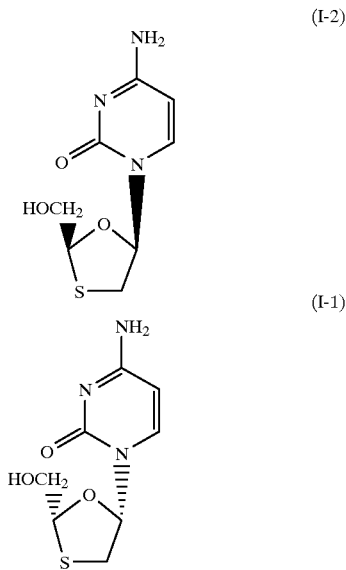

and was described and tested in the form of its racemate. The only compound currently approved for the treatment of conditions caused by HIV is 3'-azido-3'-deoxythymidine (AZT, zidovudine, BW 509U). However, this compound has a significant side-effect liability and thus either cannot be employed or, once employed, may have to be withdrawn in a significant number of patients. There is in consequence a continuing need to provide compounds which are effective against HIV but with a concomitant significantly better therapeutic index.

Although the enantiomers of the compound of formula (I) are equipotent against HIV the (−)-enantiomer has considerably lower cytotoxicity than the other enantiomer and is thus the preferred compound as an antiviral agent.

The (−)-enantiomer has the chemical name (−)cis-4-Amino-1-(2-hydroxymethyl-1,3-oxathiolan-5-yl)-(1H)-pyrimidin-2-one. It has the absolute stereochemistry of the compound of formula (I-1) which has the name (2R,cis))-4-amino-1-(2-hydroxymethyl-1,3-oxathiolan-5-yl)-(1H)-pyrimidin-2-one. The compound is now known as 3TC.

Preferably 3TC will be substantially free of the corresponding (+)-enantiomer, that is to say no more than about 5% w/w of the (+)-enantiomer, preferably no more than about 2%, in particular less than about 1% w/w is present.

International application PCT/GB91/00706, publication no WO91/17159 describes the preparation of 3TC, its antiviral activity and its use in medicine. 3TC is described and prepared in WO91/17159 as a freeze dried powder.

We have now found that 3TC can be obtained in crystalline form and exhibits polymorphism.

There is thus provided in a first aspect of the invention 3TC in crystalline form.

When crystallised from aqueous solution 3TC is obtained in the form of needle-shaped crystals (hereinafter Form I). In this form the crystals are not favoured for pharmaceutical formulation into solid dosage forms because of their physical properties, for example poor flow characteristics. We have further found that under certain conditions 3TC may be obtained in the form of substantially bipyramidal crystals (hereinafter Form II). The crystal habit of Form II has improved flow characteristics and is thus preferred in the manufacture of solid dosage forms. In addition Form I crystals are a less stable polymorphic forms and certain pharmaceutical unit operations such as milling may cause conversion of Form I to Form II, an undesirable characteristic for manufacture of solid dosage forms.

3TC in the form of bipyramidal crystals has a melting point of greater than about 170° C., in particular 177–178° C. when pure. 3TC in the form of needle-like crystals has a melting point of less than about 130° C. in particular about 124–127° C. in pure form.

3TC in Form II exhibits characteristic absorption bands in its infra red (i.r.) spectrum which are absent from the i.r. spectrum of Form I. In particular Form II exhibits strong absorption bands at ~920 and ~850 wavenumbers. Further, a characteristic band of Form I at 1110 wavenumbers is absent from the spectrum of Form II.

Form II of 3TC further shows a characteristic endotherm with an onset temperature at 177–178° C. in its differential scanning calorimetry (DSC) profile. By contrast Form I shows a characteristic endotherm in its DSC profile with an onset temperature at 124–127° C.

There is thus provided in a further aspect of the invention 3TC in the form of needle shaped crystals.

In a further aspect there is provided 3TC in the form of bipyramidal crystals.

In a yet further aspect of the invention there is provided 3TC in crystalline form and having a melting point of greater than 170° C., in particular 177–178° C. In an alternative aspect there is provided 3TC in crystalline form and having in its DSC profile an endotherm with an onset temperature of 177–178° C.

In a yet further alternative there is provided 3TC in crystalline form and having absorption bands at about 920 and about 850 wavenumbers in its infra red spectrum. In particular there is provided 3TC in which in addition to absorption bands at these wavenumbers a band at 1110 wavenumbers is substantially absent.

3TC may be obtained from its racemate by resolution by any method known in the art for the separation of racemates into their constituent enantiomers. In particular 3TC may be obtained from the known racemate by chiral HPLC, by enzyme mediated enantioselective catabolism with a suitable enzyme such as cytidine deaminase or by selective enzymatic degradation of a suitable derivative using a 5'-nucleotide. Suitable methods for preparing 3TC are described in WO91/17159.

3TC in the form of needle shaped crystals may be obtained by crystallisation of the compound from aqueous solution or by azeotropic distillation with propan-1-ol.

3TC in the form of the preferred bipyramidal shaped crystals may be obtained by recrystallisation from non-aqueous media, in particular a lower ($C_{2-6}$) alcohol, for example ethanol, IMS (industrial methylated spirit) or propan-1-ol. In a preferred method 3TC in bipyramidyl form may be obtained from 3TC in needle form by ageing the latter in Industrial Methylated Spirit (IMS) or ethanol at elevated temperature (e.g. 30–70°, particularly about 50° C.) for an appropriate time (e.g. 0.5–3 hrs, in particular about 1 hour or more).

Alternatively 3TC in bipyramidyl form may be obtained by heating the compound in needle form above its melting point of 124–127°, in particular above about 170° C., for example above about 177–178° C. and allowing the melt to cool.

In a further alternative 3TC in bipyramidyl form may be obtained by grinding or milling the compound in the form of needle shaped crystals.

Preferably 3TC is in the form of bipyramidyl shaped crystals substantially free of needle crystals. Where these crystals are obtained by recrystallisation or ageing in liquid media the compound will normally be obtained entirely free of needle shaped crystals.

3TC in crystalline form may be used as an antiviral agent, for example in the treatment of retroviral infections.

In a further or alternative aspect there is provided a method for the treatment of a viral infection, in particular an infection caused by a retrovirus such as HIV, in a mammal including man comprising administration of an effective amount of the bipyramidyl crystalline compound of the present invention.

There is also provided in a further or alternative aspect use of the bipyramidal crystalline compound for the manufacture of a medicament for the treatment of a viral infection.

The bipyramidal crystalline compound of the invention is useful in the treatment of AIDS related conditions such as AIDS-related complex (ARC), progressive generalized lymphadenopathy (PGL), AIDS-related neurological conditions (such as dementia or tropical paraparesis), anti-HIV antibody positive and HIV-positive conditions, Kaposi's sarcoma, thrombocytopenia purpurea and associated opportunistic infections for example *Pneumocystis carinii.*

The bipyramidal crystalline compound of the invention is also useful in the prevention of progression to clinical illness of individuals who are anti-HIV antibody or HIV-antigen positive and in prophylaxis following exposure to HIV.

The bipyramidal I crystalline compound may also be used for the prevention of viral contamination of physiological fluids such as blood or semen in vitro.

It will be appreciated by those skilled in the art that reference herein to treatment extends to prophylaxis as well as the treatment of established infections or symptoms.

It will be further appreciated that the amount of the bipyramidAl crystalline compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, the bipyramidAl crystalline compound of the invention my be administered as the raw chemical it is preferable to formulate it into a pharmaceutical formulation.

The invention thus further provides a pharmaceutical formulation comprising the bipyramidal crystalline compound together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-linqual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and the, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The bipyramidal crystalline compound according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the bipyramidal crystalline compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the bipyramidal crystalline compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more dispersing agents, solubilishing agents or suspending agents. Liquid sprays are conveniently delivered from pressurized packs.

For administration by inhalation the bipyramidal crystalline compound according to the invention is conveniently delivered from an insufflator, nebuliser or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the bipyramidal crystalline compound according to the invention may take the form of a dry powder composition, for example a powder mix of the compound and a suitable powder base such a lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other antiinfective agents. In particular the compounds of the invention may be employed together with known antiviral agents.

The invention thus provides, in a further aspect, a combination comprising the bipyramidal crystalline compound together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

Suitable therapeutic agents for use in such combination include acyclic nucleosides such as acyclovir or ganciclovir, interferons such as α, β or γ-interferon, renal excretion inhibitors such as probenecid, nucleoside transport inhibitors such as dipyridamole, 2',3'-dideoxynucleosides such as AZT, 2',3'-dideoxycytidine, 2',3'-dideoxyadenosine, 2',3'-dideoxyinosine, 2',3'-dideoxythymidine, 2',3'-dideoxy-2',3'-didehydrothymidine and 2',3'-dideoxy-2',3'-didehydrocytidine, immunomodulators such as interleukin II (IL2) and granulocyte macrophage colony stimulating factor (GM-CSF), erythropoetin, ampligen, thymomodulin, thymopentin, foscarnet, ribavirin and inhibitors of HIV binding to CD4 receptors e.g. soluble CD4, CD4 fragments, CD4 hybrid molecules, glycosylation inhibitors such as 2-deoxy-D-glucose, castanospermine and 1-deoxynojirimycin.

The individual components of such combinations may be administered either sequentially or simultaneously in separate or combined pharmaceutical formulations When the bipyramidal crystalline compound is used in combination with a second therapeutic agent active against the same virus the dose of each compound may be either the same as or differ from that when the compound is used alone. Appropriate doses will be readily appreciated by those skilled in the art.

FIG. 5 is a DSC thermogram of Form I crystals.

FIG. 6 is a DSC thermogram of Form II crystals.

Figure 1:
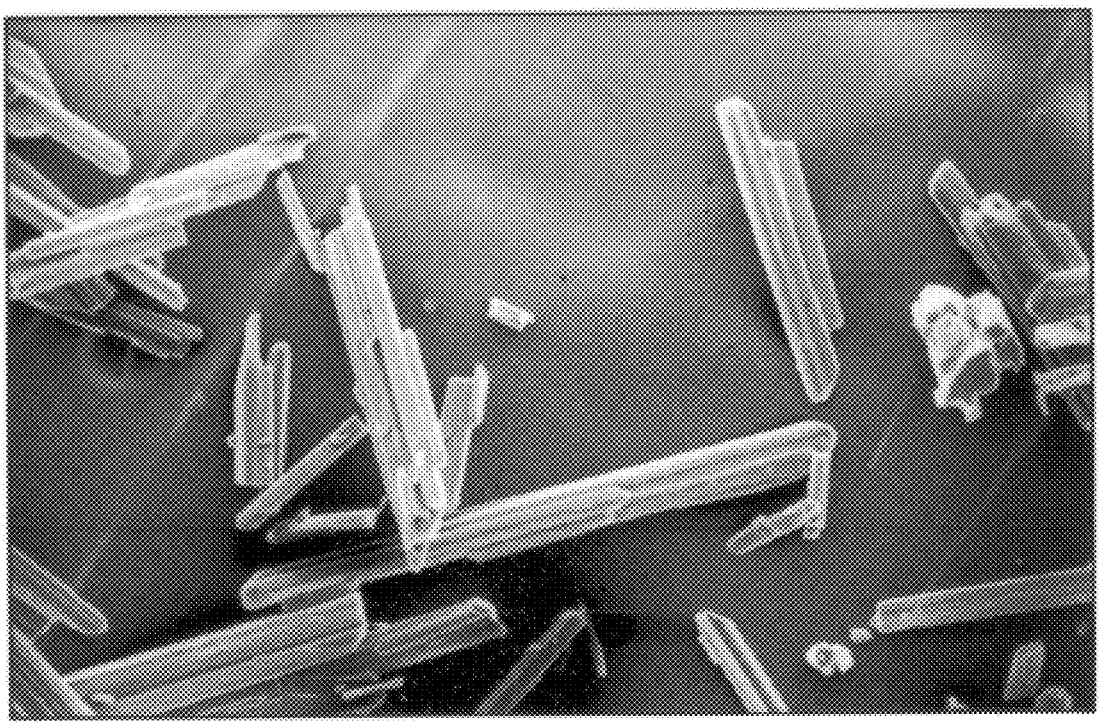
FIG. 1 shows 3TC in the form of needle shaped crystals (Form I).
Figure 2:
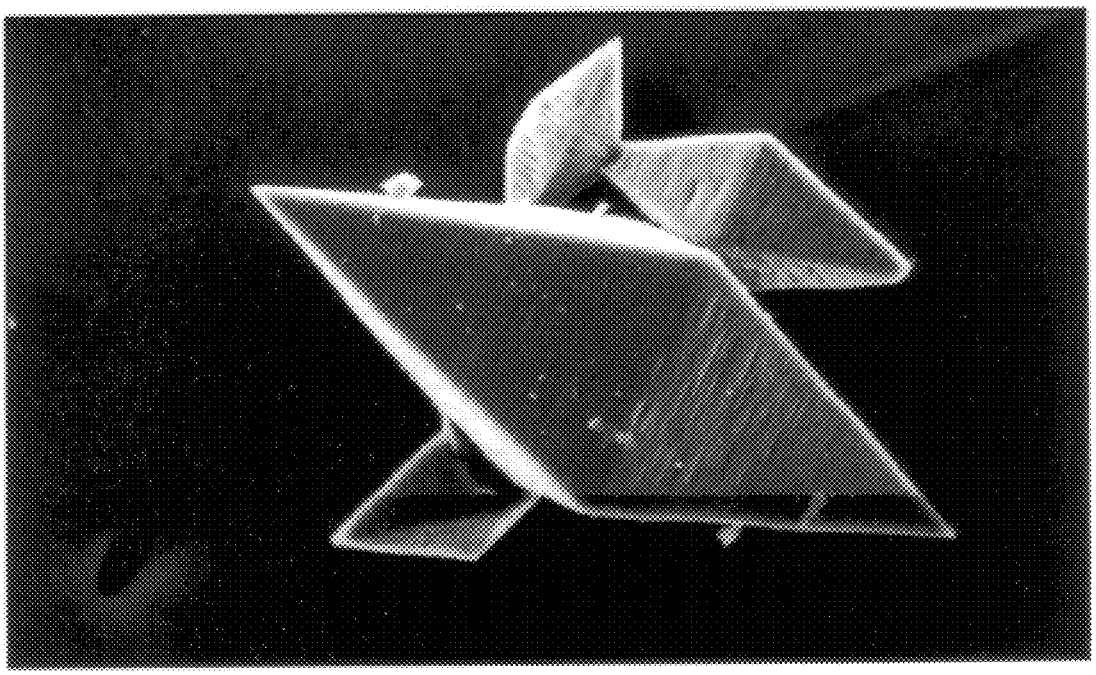
FIG. 2 shows 3TC in the form of bipyramidal shaped crystals (Form II).

The following examples illustrate the invention but are not intended as a limitation thereof. All temperatures are in ° C.

INTERMEDIATE 1

5-Methoxy-1,3-oxathiolane-2-methanol, benzoate

A solution of zinc chloride (1.6 g) in hot methanol (15 ml) was added to a stirred solution of mercaptoacetaldehyde, dimethyl acetal (34.2 g) and benzoyloxy acetaldehyde (48.3 g) in toluene (1300 ml) which was then heated to reflux under nitrogen for 50 min. The cooled mixture was concentrated, diluted with some toluene, then filtered through Kieselguhr. The combined filtrates and toluene were washed with aqueous saturated sodium bicarbonate solution (×2) and brine, dried (MgSO$_4$) then evaporated to an oil which was subjected to column chromatography on silica (2 kg, Merck 9385 ) eluted with chloroform to give the title product as an oil (45.1 g) a mixture of anomers (ca 1:1); 1H NMR (DMSO-d$_6$) 3.1–3.3(4H), 3.42(6H), 4.4–4.6 (4H), 5.41(1H), 5.46 (1H), 5.54 (1H), 5.63 (1H ), 7.46 (4H), 7.58 (2H), 8.07 (4H);λ max (CHBr$_3$)1717.6 cm$^{-1}$.

INTERMEDIATE 2

(±)-cis-1-(2-Benzoyloxymethyl-1,3-oxathiolan-5-yl)-(1H)-pyrimidin-2-4-dione

A mixture of finely ground uracil(9.62 g) hexamethyl disilazane (50 ml) and ammonium sulphate (30 mg) was heated at reflux under nitrogen until a clear solution was obtained. This was cooled and then evaporated to a colourless oil, which was dissolved, under nitrogen atmosphere, in acetonitrile (100 ml). The solution was added to a stirred ice cooled solution of 5-methoxy-1,3-oxathiolane-2-methanol, benzoate (intermediate 1) (19.43 g), in acetonitrile (600 ml) and trimethyl silyl trifluoromethanesulphonate (14.7 ml) was added. The ice bath was removed, and the solution was heated at reflux under nitrogen for 45 mins. After cooling and evaporation, the residue was purified by column chromatography over 1 kg of silica gel (Merck 9385) eluting with chloroform/methanol 9:1. Appropriate fractions were cooled and evaporated to afford a crude residue. This was fractionally crystallized from the minimum of hot methanol (c.1200 ml) to afford the title compound (6.32 g) as white crystals. 1H NMR( d°DMSO) δ 11.36 (1H,bs). 7.50–8.00 (6H,m), 6.20 (1H,t), 5.46 (2H,m), 4,62 (2H, m), 3.48 (1H, m), 3.25 (1H, m).

INTERMEDIATE 3

(±)-(cis)-4-Amino-1-(2-benzoyloxymethyl-1,3-oxathiolan-5-yl)-(1H)-pyrimidin-2-one Method (a)

A suspension of cytosine (20.705 g) and ammonium sulphate (few mgs) in hexamethyldisilazane (110 ml) was stirred and heated at reflux for 2½ h, under nitrogen. Solvent was removed by evaporation, and the residual solid was dissolved in dry acetonitrile (350 ml). This solution was transferred using flexible needle techniques into a stirred, ice-chilled solution of 5-methoxy-1,3-oxathiolane-2-methanol, benzoate (Intermediate I) (43.57 g) in acetonitrile (650 ml) under nitrogen. Trimethylsilyl trifluoromethanesulphonate (33 ml) was added, the solution was allowed to warm to ambient temperature (1½ h) then heated to reflux for an overnight period. The residue mixture was concentrated, diluted with saturated aqueous sodium bicarbonate solution (500 ml), then extracted with ethyl acetate (3×500 ml). The combined extracts were washed with water (2×250 ml) and brine (250 ml) dried (MgSO$_4$) then evaporated to a foam which was subjected to column chromatography on silica (600 g, merck 7734), eluted with ethyl acetate-methanol mixtures to give a mixture of anomers (ca 1:1 31.59 g). The mixture was crystallised from water (45 ml) and ethanol (9.0 ml) to give a solid (10.23 g) which was recrystallised from ethanol (120 ml) and water (30 ml) to give the title product as a white solid (9.26 g);λ max (MeOH) 229.4 mm (E$^{1\%}$ 610); 272.4 mm (E$^{1\%}$ 1 cm 1 cm 293); $^1$H NMR (DMSO d6) δ 3.14 (1H), 3.50 (1H), 4.07 (2H), 5.52 (1H), 5.66 (1H), 6.28 (1H), 7.22 (2H), 7.56 (2H), 7.72 (2H), 8.10 (2H).

Method (b)

Phosphorus oxychloride (7.0 ml) was added dropwise to a stirred, ice-cooled suspension of 1,2,4-triazole (11.65 g) in acetonitrile (120 ml) then, keeping the internal temperature below 15° C., triethylamine (22.7 ml) was added dropwise. After 10 min a solution of (±)-cis-1-(2-benzoyloxymethyl-1,3-oxathiolan-5-yl)-(1H)-pyrimidin-2,4-dione (Intermediate 2) (6.27 g) in acetonitrile (330 ml)was slowly added. Stirring was then continued at room temperature overnight. The mixture was cooled by means of an ice bath and triethylamine (30 ml) was slowly added followed by water (21 ml). The resultant solution was evaporated, and the residue was partitioned between saturated sodium bicarbonate solution (400 ml) and chloroform (3×200 ml). The combined chloroform extracts were dried and magnesium sulphate, filtered and evaporated to give a crude residue (9.7 g). The residue was dissolved in 1,4-dioxan (240 ml) and concentrated aqueous ammonia solution (s.g 0.880, 50 ml) was added. After 1½ h the solution was evaporated and the residue dissolved in methanol. This caused precipitation of a solid, which was filtered off. The mother liquors were purified by column chromatography over silica gel (Merck 9385, 600 g). Appropriate fractions were pooled and evaporated to give the title compound as a fawn solid (2.18 g), identical to that obtained by Method (a).

INTERMEDIATE 4

(±)-(cis)-4-Amino-1-(2-hydroxymethyl-1,3-oxathiolan-5-yl)-(1H)-pyrimidin-2-one

A suspension of (cis)-4-amino-1-(2-benzoyloxymethyl-1,3-oxathiolan-5-yl)(1H)-pyrimidin-2-one (Intermediate 3) (8.19 g) and Amberlite IRA-400 (OH) resin (8.24 g) in methanol (250 ml) was stirred and heated to reflux for 1¼ h. Solids were removed by filtration then washed with methanol. The combined filtrates were evaporated. The residue was triturated with ethyl acetate (80 ml). The resulting white solid was collected by filtration to give the title product (5.09 g), 1H NMR (DMSO-d$_6$) 3.04 (1H), 3.40 (1H), 3.73 (2H), 5.18 (1H), 5.29 (1H), 5.73 (1H), 6.21 (1H), 7.19 (2H), 7,81 (1H).

INTERMEDIATE 5

(−)-cis-4-Amino-1-(2-hydroxymethyl-1,3-oxathiolan-5-yl)-(1H)pyrimidin-2-one (i) Three 50 ml flasks of nutrient broth (Oxoid Ltd) were inoculated with a loopful each of *Escherichia coli* (ATCC 23848) scraped from a Nutrient Agar plate. The flasks were incubated overnight at 37° C. with shaking at 250 rev/min and then each flask was used to inoculate 4l of CDD medium (glutamic acid, 3 g/1; MgSO$_4$, 0.2 g/1: K$_2$SO$_4$, 2.5 g/1; NaC1, 2.3 g/1,Na$_2$HPO$_4$2H$_2$O, 1.1 g/1, NaH$_2$PO$_4$2H$_2$O 0.6 g/l cytidine, 1.2 g/l) in a seven liter fermenter. The cultures were fermented at 750 rev/min, 37° C. with aeration at 4l/min. After growth for 24hrs the cells were collected by centrifugation (5000 g, 30 minutes) to yield 72 g wet weight. The cell pellet was resuspended in 300 ml of 20 mM Tris HCl buffer (pH 7.5) and disrupted by sonication (4×45 seconds). The cell debris was removed by centrifugation (30,000 g, 30 minutes) and the protein in the supernatant was precipitated by addition of ammonium sulphate to 75% saturation. The precipitate was collected by centrifugation (30, 000 g. 30 minutes) and the pellet was resuspended in 25 ml of HEPES buffer (100 mM, pH 7.0) containing ammonium sulphate (75% saturation). Enzyme solution was prepared by centrifugation at 12,000 rpm for 30 mins. The supernatant was discarded and the pellet dissolved in Tris HCl buffer (pH 7.0; 100 mM) to the original volume.

(ii) Intermediate 4 (115 mg) was dissolved in water (100 ml), and stirred. Enzyme solution (0.5 ml) was added, and the mixture was maintained at a constant pH by the continual addition of HCl (25 mM). The conversion was monitored by chiral HPLC, which showed that the (+) enantiomer of the substrate was preferentially deaminated. After 22 hr the (+) enantiomer of the substrate (RT 12.5 min) had been completely removed, and the solution was adjusted to pH 10.5 by the addition of conc. sodium hydroxide.

The solution produced above was eluted through a column of QAE Sephadex (A25; Pharmacia; 30×1.6 cm), pre-equilibrated to pH11. The column was washed with water (200 ml) and then with HCl (0.1M). Fractions (40 ml) were taken, and analysed by reversed phase HPLC. Fractions 5–13, containing the unreacted (−) enantiomer of the substrate, were combined and adjusted to pH 7.5 with HCl. Fraction 47, containing deaminated product, was adjusted to pH7.5 with dil. NaOH. Analysis by chiral HPLC showed that this material was a mixture, consisting of one enantiomer (RT 10.2 min) as the major component with the other enantiomer (RT 8.5 min) as a minor component (e.e ca 90%).

(iii) Stage (ii) above was repeated on a larger scale. The compound of Example 1 (363 mg) in 250 ml of water was incubated with enzyme solution (0.5 ml), prepared as in Stage (i). Further aliquots (0.5 ml) of enzyme were added after 18 and 47 hrs. The reaction mixture was stirred for 70 hr., then left standing for a further 64 hr. Analysis by chiral hplc indicated that the (+) enantiomer of the substrate had been completely deaminated, and the resulting solution was adjusted to pH10.5 with NaOH.

The solution above was loaded onto the same QAE column, and eluted as in stage (i). Fractions 2–6, containing a mixture of the residual substrate and deaminated product, were bulked. Fractions 7–13, containing the residual substrate ((−) enantiomer), were bulked and adjusted to pH7.5. Fractions 25–26, containing deaminated product, were bulked and neutralised Fractions 2–6 above were re-eluted through the same QAE column. Fractions 3–11 from this second column contained unrected substrate-((−) enantiomer). Fraction 70 contained the deaminated product.

(iv) The resolved substrate fractions from stage (ii) and (iii) were combined and adjusted to pH7.5. This solution was eluted through a column of XAD-16 (40×2.4 cm), packed in water. The column was washed with water, and then eluted with acetone: water (1:4 v/v). Fractions containing the desired (−) enantiomer were bulked and freeze-dried to give a white powder (190 mg).

The HPLC methods used above were as follows:

1. Reversed Phase analytical HPLC

| | |
|---|---|
| Column | Capital Cartridge |
| | Spherisorb ODS-2 (5 uM) |
| | 150 × 4.6 mm |
| Eluant | Ammonium dihydrogen phosphate (50 mM) + |
| | 5% MeCN |
| Flow | 1.5 ml/min |
| Detection | UV, 270 nm |
| Retention Times | BCH 189 5.5 min |
| | deaminated BCH −189 8.1 min |

2. Chiral analytical HPLC

| | |
|---|---|
| Column | Cyclobond I Acetyl |
| | 250 × 4.6 mm |
| Eluant | 0.2% Triethylammonium acetate (pH 7.2) |
| Flow | 1.0 ml/min |
| Detection | UV, 270 nm |
| Retention Times | BCH 189 11.0 and 12.5 min |
| | deaminated BCH-189 8.5 and 10.2 min |
| | (The bioconversion was followed by monitoring the loss of the peak at 12.5 min., and accumulated of product at 10.2 min). |

Example 1

A suspension of Intermediate 5 (64.8 g) in water (200 mL) was heated to 45° to give a solution. The solution was cooled to 30 °.

The product crystallised as an unstirrable mass. This was broken up and the suspension stirred at ca. 10° for 1 h.

The product was isolated by filtration and washed with ethanol (IMS; 2×30 mL) then dried in vacuo at 45° for 24 h to give 3TC as Form I (fine needle crystals).

Figure 3:
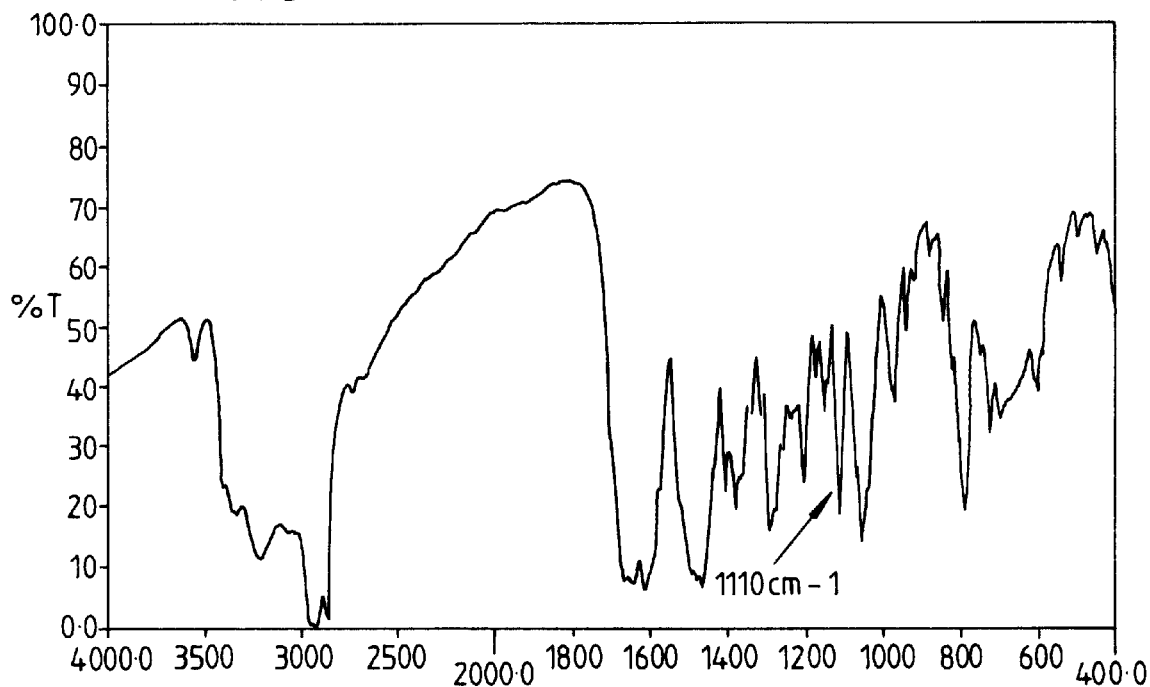
FIG. 3 is an infra-red spectrum of Form I crystals.

The compound had an i.r. spectrum and DSC thermograph identical to FIGS. 3 and 5 respectively.

Example 2

A suspension of the compound of Example 1 (10.0 g) in industrial methylated spirits (IMS; 200 mL; 20 volumes) was heated to reflux to give a clear solution. The solution was filtered hot and the filtrate was distilled at atmospheric pressure until 100 mL (10 volumes) of solution remained. The solution was seeded with authentic material[2] and allowed to cool from 80° to 25° over 1 h. Crystallisation began at 79°. The suspension was stirred at 15° for 1 h. The product was isolated by filtration and washed with IMS (10 mL; 1 volume). Drying in vacuo at 50° gave the title compound as aggregates of bipyramides (8.42 g) m.p. 179–181°. (−)-cis-4-amino-1-(2-hydroxymethyl-1,3-oxathiolan-5-yl)-(1H)-pyrimidin-2-one. Assay Found: C,41.9; H,4.85; N,18.35 $C_8H_{11}N_3O_3S$ requires: C,41.9; H,4.8; N,18.3%

Figure 4:
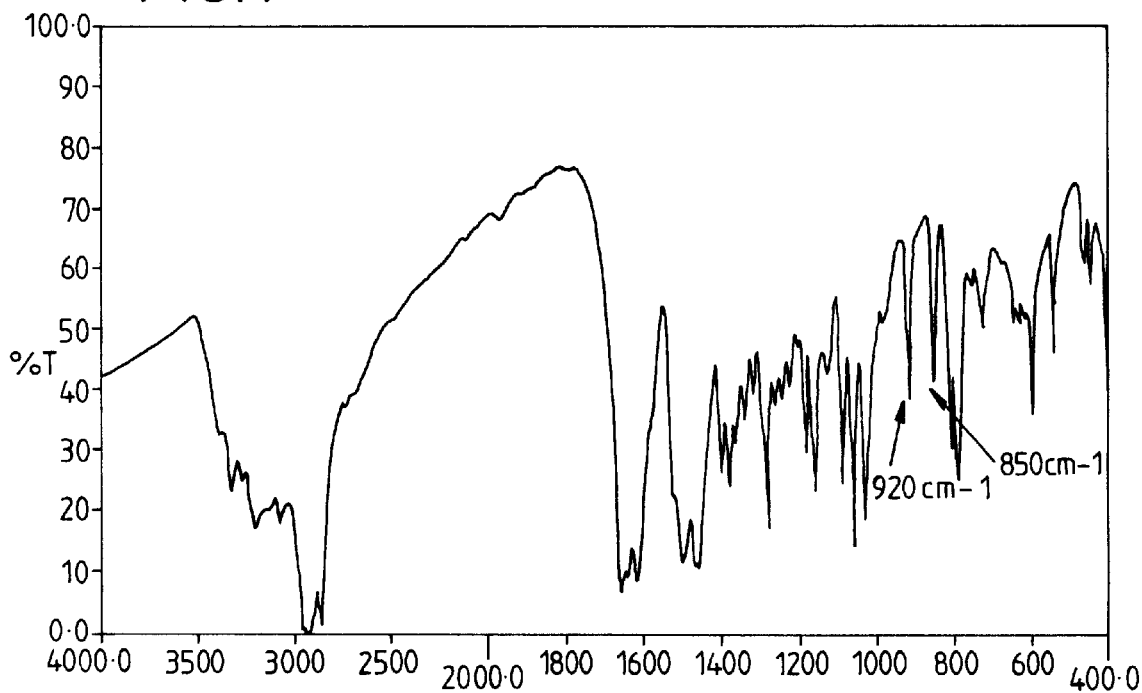
FIG. 4 is an infra-red spectrum of Form II crystals.

The compound had an i.r. spectrum and DSC thermograph identical to FIGS. 4 and 6 respectively.

Example 3

A suspension of the product of Example 1 (20.0 g) in Industrial Methylated Spirits (IMS; 100 mL; 5 volumes) was stirred slowly at 50 ° for 1 h.

A small sample (ca 100 mg) was removed, dried in vacuo at 50 ° and examined by microscopy and differential scanning calorimetry (DSC).

The sample was 100% Form II (bipyramidal habit).

The suspension was stirred at 50 ° for a further 2 h and a sample removed. Microscopy showed no change.

The suspension was stirred at 50 ° for 22 h, then cooled to 20 ° and stirred for 1 h.

The suspension was filtered, the product washed with IMS (20 mL; 1vol) and dried in vacuo to give as a white crystalline solid (17.13 g) (−)-cis-4-amino-1-(2-hydroxymethyl-1,3-oxathiolan-5-yl)-(1H)-pyrimidin-2-one m.p. 180–181°. Assay Found: C,41.85; H,4.85; N,18.3 $C_8H_{11}N_3O_3S$ Requires: C,41.9; H,4.8; N,18.3%

The product had an i.r. spectrum and DSC thermogram identical to those of FIGS. 4 and 6 respectively.

Example 4

X-Ray Crystallography data for Form II
Crystal Data:
$C_8H_{11}N_3O_3S, M=229.26$.

Tetragonal, $a=b=8.749(3)$, $c=26.523(9)$A, $V=2030(2)$A$^3$ (by least-squares refinement on diffractometer angles for 14 automatically centred reflections, $1=1.54184$A).

Space group $P4_32_12$ (No. 96), $z=8$, $DC=1.50$ g cm$^{-3}$.
$F(000)=960$, $m(Cu-Ka)=27.5$ cm$^{-1}$.
Dimensions of data crystal $0.48\times0.32\times0.30$ mm.

Single crystals of Form II (colourless bipyramids) were examined by X-ray diffraction. A total of 1651 reflections were measured ($3<2J<115°$) on a Siemens R$^3$ m/V diffractometer with monochromatised Cu-Ka radiation and using 2J/w scans. The structure was solved by direct methods and the non-hydrogen atoms refined anisotropically. The hydrogen atoms attached to carbon were idealised (C-H=0.96A) and allowed to ride on their parent carbon atoms. Three Hs on —NH$_2$ and —OH groups were located from a difference Fourier map. All H atoms were refined isotropically. Refinement converged to give $R=0.068$, $R_w=0.069$, $w^{-1}=[s^2(F)+0.005[F]^2]$. Maximum residual electron density was 0.45 eA$^{-3}$. The absolute chirality was confirmed using Rogers' eta test [h=0.99(9)].

Example 5

Pharmaceutical Formulations
(a) 100 mg Tablets

| Ingredients per tablet | |
|---|---|
| 3TC (Form II) | 100.0 mg |
| Microcrystalline Cellulose NF | 189.5 mg |
| Sodium Starch Glycolate NF | 9.0 mg |
| Magnesium Stearate NF | 1.5 mg |
| Total Weight | 300.0 mg |

The 3TC (Form II), microcrystalline cellulose and sodium-starch glycolate were sieved and blended in a V-blender for about 15 minutes. Sieved magnesium stearate was then added and blending continued for a further 2 minutes.

The blend was compressed in standard tabletting equipment and then film coated with an aqueous suspension of grey Opadry to produce aesthetically acceptable tablets.

(b) 300 mg Tablets

| Ingredients per tablet | |
|---|---|
| 3TC (Form II) | 300.0 mg |
| Microcrystalline Cellulose NF | 279.0 mg |
| Sodium Starch Glycolate NF | 18.0 mg |
| Magnesium Stearate NF | 1.5 mg |
| Total Weight | 600.0 mg |

Tablets were prepared as described in (a) above.

We claim:

1. A pharmaceutical formulation in solid dosage unit form comprising an effective amount of (-)-cis-4-amino-1-(2-hydroxymethyl)-1,3-oxathiolan-5-yl)-(1H)pyrimidine-2-one in bipyramidal crystalline form and a pharmaceutically acceptable carrier therefor.

2. A pharmaceutical formulation as claimed in claim 1 in the form of a tablet or capsule.

3. (-)-cis-4-Amino-1-(2-hydroxymethyl-1,3-oxathiolan-5-yl)-(1H)-pyrimidin-2-one in the form of bipyramidyl crystals.

4. The crystalline form as claimed in claim 3 having a melting point of greater than 170° C.

5. The crystalline form as claimed in claim 3, having a melting point of 177–178° C.

6. The crystalline form as claimed in claim 3 having absorption bands in its infra-red spectrum of 920 and 850 wave numbers.

7. The crystalline form as claimed in claim 3 having no absorption band in its infra-red spectrum at 1110 wave numbers.

8. The crystalline form as claimed in 3 having an endotherm with an onset temperature at 177–178° C. in its differential scanning calorimetry profile.

9. A pharmaceutical composition in solid dosage unit form consisting essentially of a therapeutically effective amount (-)-cis-4-amino-1-(2-hydroxymethyl-1,3-oxathiolan-5-yl)-(1H)-pyrimidin-2-one in bipyramidyl crystalline form in combination with a pharmaceutically acceptable carrier therefor.

10. A pharmaceutical composition in solid dosage unit form comprising a therapeutically effective amount of (-)-cis-4-amino-1-(2-hydroxymethyl-1,3-oxathiolan-5-yl)-(IH)-pyrimidin-2-one in bipyramidal crystalline form in combination with a pharmaceutically acceptable carrier therefor.

11. A pharmaceutical composition according to claim 10 where in the (-)-cis-4-amino-1-(2-hydroxymethyl-1,3-oxathiolan-5-yl)-(IH)-pyrimidin-2-one in bipyramidal crystalline form is substantially free of non-crystalline (-)-cis-4-amino-1-(2-hydroxymethyl-1,3-oxathiolan-5-yl)-(IH)-pyrimidin-2-one.

12. A pharmaceutical composition according to claim 10 wherein the (-)-cis-4-amino-1-(2-hydroxymethyl-1,3-oxathiolan-5-yl)-(IH)-pyrimidin-2-one in bipyramidal crystalline is substantially free of needle crystals of (-)-cis-4-amino-1-(2-hydroxymethyl-1,3-oxathiolan-5-yl)-(IH)-pyrimidin-2-one.

13. A pharmaceutical composition according to claim 10 in oral administration form.

14. A pharmaceutical composition useful for treating HIV infections in humans which comprises a therapeutically effective amount of a combination of 3'-azido-3'-deoxythymidine (AZT) and (-)-cis-4-amino-1-(2-hydroxymethyl-1,3-oxathiolan-5-yl)-IH-pyrimidin-2-one in bipyramidal crystalline form, in combination with a pharmaceutically acceptable carrier.

15. A pharmaceutical composition useful for treating HIV infections in humans which comprises a therapeutically effective amount of a combination of 3'-azido-3'-deoxythymidine (AZT) and (-)-cis-4-amino-1-(2-hydroxymethyl-1,3-oxathiolan-5-yl)-IH-pyrimidin-2-one in bipyramidal crystalline form substantially free of non-crystalline (-)-cis-4-amino-1-(2-hydroxymethyl-1,3-oxathiolan-5yl)-(IH)-pyrimidin-2-one, in combination with a pharmaceutically acceptable carrier.

16. A pharmaceutical composition useful for treating HIV infections in humans which comprises a therapeutically effective amount of a combination of 3'-azido-3'-deoxythymidine (AZT) and (-)-cis-4-amino-1-(2-hydroxymethyl-1,3-oxathiolan-5-yl)-1H-pyrimidin-1-one in bipyramidal crystalline form substantially free of needle crystals, in combination with a pharmaceutically acceptable carrier.

17. A pharmaceutical composition according to claim 14 in oral administration form.

18. A pharmaceutical composition according to claim 17 in tablet form.

19. A pharmaceutical composition according to claim 17 in capsule form.

20. A method of treating HIV infections in humans which comprises administering to a human in need thereof a therapeutically effective amount of 3'-azido-3'-deoxythymidine (AZT) and (−)-cis-4-amino-1-(2-hydroxymethyl-1,3-oxathiolan-5yl)-IH-pyrimidin-2-one in bipyramidal crystalline form, in combination with a pharmaceutically acceptable carrier.

21. A method of treating HIV infections in humans which comprises administering to a human in need thereof a therapeutically effective amount of 3'-azido-3'-deoxythymidine (AZT) and (−)-cis-4-amino-1-(2-hydroxymethyl-1,3-oxathiolan-5yl)-IH-pyrimidin-2-one in bipyramidal crystalline form substantially free of non-crystalline (−)-cis-4-amino-1-(2-hydroxymethyl-1,3-oxathiolan-5yl)-IH-pyrimidin-2-one, in combination with a pharmaceutically acceptable carrier.

22. A method of treating HIV infections in humans which comprises administering to a human in need thereof a therapeutically effective amount of 3'-azido-3'-deoxythymidine (AZT) and (−)-cis-4-amino-1-(2-hydroxymethyl-1,3-oxathiolan-5yl)-IH-pyrimidin-2-one in bipyramidal crystalline form substantially free of needle crystals of (−)-cis-4-amino-1-(2-hydroxymethyl-1,3-oxathiolan-5yl)-IH-pyrimidin-2-one, in combination with a pharmaceutically acceptable carrier.

23. A method according to claim 20 wherein the administration is sequential.

24. A method according to claim 20 wherein the administration is simultaneous.

25. A method according to claim 20 wherein the administration is oral.

26. A method according to claim 25 wherein the oral administration is in tablet form.

27. A method according to claim 25 wherein the oral administration is in capsule form.

* * * * *